United States Patent [19]

Garrett et al.

[11] 4,197,848

[45] Apr. 15, 1980

[54] CLOSED URINARY IRRIGATION SITE

[75] Inventors: Scott T. Garrett, Highland Park; Robert R. Fasana, Antioch; William L. Rudzena, Fox Lake, all of Ill.

[73] Assignee: Baxter Travenol Laboratories, Inc., Deerfield, Ill.

[21] Appl. No.: 867,404

[22] Filed: Jan. 6, 1978

[51] Int. Cl.$^2$ ............................................. A61M 7/00
[52] U.S. Cl. .................................. 128/247; 128/349 R
[58] Field of Search ................... 128/247, 275, 214 D, 128/349 R, 350 R, 350 V, DIG. 24, 349 BV, 274

[56] References Cited

U.S. PATENT DOCUMENTS

| | | | |
|---|---|---|---|
| 3,478,743 | 11/1969 | Ericson | 128/349 BV |
| 3,577,992 | 5/1971 | Merry et al. | 128/349 BV |
| 3,598,124 | 8/1971 | Anderson et al. | 128/275 |
| 3,741,217 | 6/1973 | Ciarico | 128/349 R |

FOREIGN PATENT DOCUMENTS

| | | | |
|---|---|---|---|
| 964544 | 3/1975 | Canada | 128/349 BV |
| 35387 | 2/1965 | German Democratic Rep. | 128/274 |
| 1078650 | 8/1967 | United Kingdom | 128/349 BV |

Primary Examiner—Robert E. Bagwill
Attorney, Agent, or Firm—Paul C. Flattery; John P. Kirby, Jr.; Garrettson Ellis

[57] ABSTRACT

An improved closed irrigation site in a urinary irrigation device. The site is characterized by a rigid lip defining a mouth at the distal end of an irrigation tube, a resilient, impervious membrane against the lip and covering the mouth and having a normally closed, resiliently deformable slit therethrough over the mouth, and a plug or other member securing the membrane against the lip. In preferred embodiments, the membrane is compressed against the lip thereby biasing the slit in a closed position. Other preferred embodiments relate to unique structure providing specific benefits.

12 Claims, 4 Drawing Figures

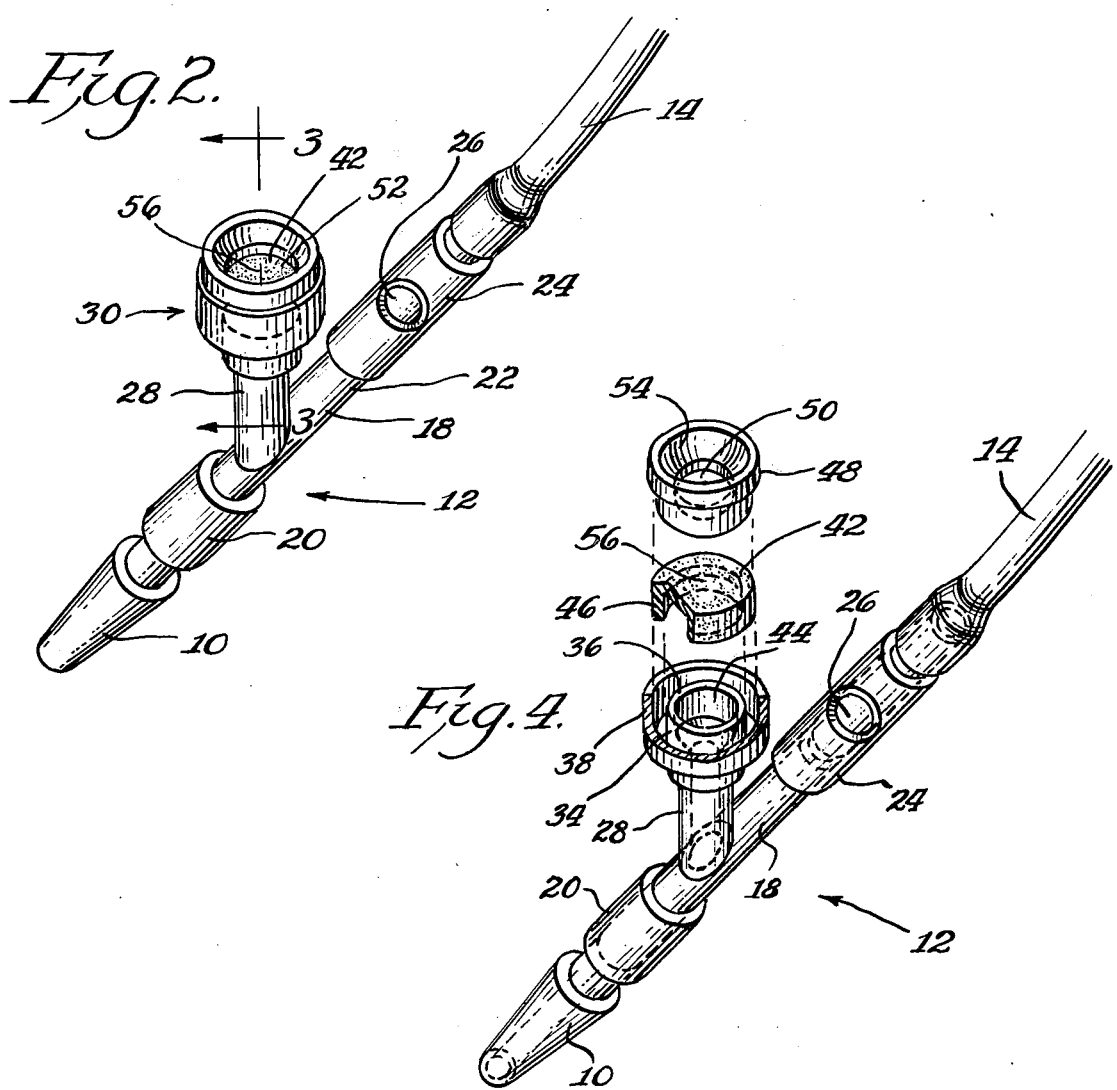
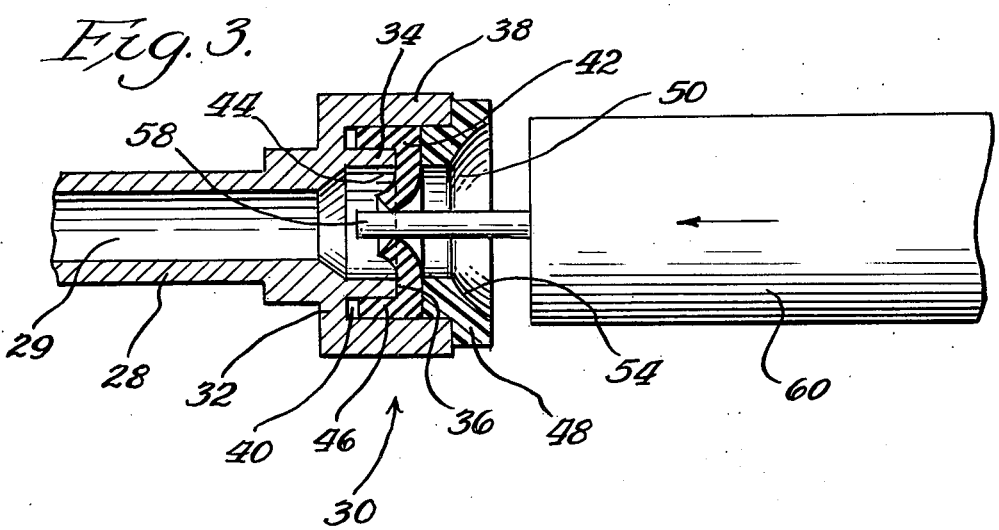

CLOSED URINARY IRRIGATION SITE

BACKGROUND OF THE INVENTION

This invention relates to urinary irrigation devices, and, more particularly, to closed irrigation sites for urinary drainage systems.

A long-term urinary drainage system typically has a self-retaining catheter, drainage tubing, and a collection bag, all in fluid communication. Such urinary drainage systems require periodic irrigation of the catheter with a sterile normal saline solution or water, to prevent blood clots and the like from obstructing the system. Common irrigation practice has required a break in the closed drainage system, which, of course, allows the entrance of air which may carry contaminates into the closed system, creating the possibility of infection. Medical studies have shown that urinary tract infections during catherization are widespread, particularly after a catheter remains indwelling for several days.

Various attempts have been made to reduce or eliminate the likelihood of infection. Such measures have included improvement of the design of catheters, use of prophylactic antibiotics, attempts to maintain a completely closed system, and the use of closed irrigation access sites through which an irrigant is introduced.

Some urinary drainage devices provide irrigation without ever breaking the closed system. For example, some systems have utilized continuous attachment of an irrigation set. This sort of device, however, is bulky and prevents freedom of movement for ambulatory patients.

More recent devices have included closed irrigation access sites through which an irrigant may periodically be introduced. One of such devices, commonly called irrigation valves, is that shown in U.S. Pat. Nos. 3,577,992 and 3,965,910. Such irrigation valves are difficult or impossible to properly disinfect or "prep" prior to irrigation. The inherent complexity of design of such valves provides corners, spaces, and gaps which cannot be cleaned thoroughly, and, therefore, provide an opportunity for bacterial growth. The bacteria, rather than being disinfected, are washed into the system and into the patient. Such devices have the further disadvantage of their internal structure tending to impede the flow of irrigating fluid from the syringe source to the bladder. Furthermore, in some cases the structure will impede the normal drainage flow from the bladder to the collection bag.

Needle injection sites cannot advantageously be used for irrigation purposes because, while such sites would eliminate introduction of contaminated air, they would not allow a sufficient flow of irrigating fluid.

Devices such as that disclosed in U.S. Pat. No. 3,994,293 (Ferro), while allowing greater flow, would impede the flow of irrigant from a syringe source. Furthermore, such devices are difficult to properly prep, having an area which is exposed to the air but nearly inaccessible to swabbing.

BRIEF SUMMARY OF THE INVENTION

This invention provides an improved close irrigation site in a urinary irrigation device overcoming the aforementioned problems of the prior art. The site is generally at the distal end of a tubular irrigation branch attached to a main tubular member which forms part of a urinary drainage path. As with devices of the prior art, the upstream or inlet end of the main tubular member is suitably connected to a catheter which leads to a bladder, and the downstream or outlet end of the main tubular member is suitably connected to tube means which leads to a collection bag. The irrigating fluid is fed into the system at the closed irrigation site and reaches the main drainage path through the tubular branch.

The closed irrigation site of this invention is characterized by a rigid lip at the distal end of the tubular branch, which lip defines a mouth, a resilient, impervious membrane against the lip and covering the mouth and having a normally closed, resiliently deformable slit therethrough over the mouth, and a plug or other member securing the membrane against the lip.

The present invention provides an irrigation access site, namely, the slit membrane, which can be penetrated by a blunt syringe tip to deliver irrigating fluid into the system without any impedance caused by the site at the point of introduction. The slit may be deformed to allow temporary entry of such blunt syringe tip, but the membrane material characteristics of deformability and resiliency, in such mounted membrane, cause the slit to close about the tip thereby keeping the system substantially closed to contaminating air even during introduction of irrigating fluid. When the blunt syringe is withdrawn, the slit immediately closes upon itself due to the resilient nature of the membrane material. Thus, such access site remains closed and bars air passage before, after and during protrusion of the syringe tip therethrough.

In a preferred embodiment, the membrane is compressed in sandwich fashion against the lip thereby biasing the slit in a tightly closed position. Such compression has the effect of producing radially inward forces within the membrane, directed generally toward the slit, to assure the proper operation thereof.

The slit is preferably substantially straight. A straight slit readily receives and closes about the blunt end of a syringe, and closes tightly upon itself when the syringe is withdrawn.

In certain preferred embodiments, an apertured plug which secures the membrane against the lip forms an exposed annular surface tapered inwardly substantially to the membrane, free of crevices and the like, to provide an irrigation access site which may easily be cleansed or prepped prior to irrigation. Such cleansing may readily be accomplished by even unskilled personnel, by swabbing or otherwise. This feature minimizes or eliminates external crevices or other areas in which bactera could accumulate.

In a highly preferred structure, the distal end of the tubular branch includes an enlarged base projecting radially from the axis of the branch and two generally concentric, substantially cylindrical annuli projecting axially in an upstream direction. The annulus of larger diameter, that is, the outer annulus, projects axially beyond the inner annulus. These two annuli define a substantially cylindrical, annular void therebetween. In such an embodiment, the membrane member has an integral skirt received within such void, and is thereby kept in secure and proper orientation at all times. An axially apertured plug member is received into the outer annulus and connected thereto.

It is highly preferred that the main tubular member and the tubular branch of the urinary drainage device be an integral, rigid structure. Such a structure provides for ease of use. It is also preferred that the tubular branch form an obtuse angle with the upstream portion of the main tubular member. Such configuration serves to direct the irrigating fluid upstream to the catheter when such fluid is introduced.

The urinary irrigation device of this invention is simple in construction, and does not impede either the flow of irrigating fluid during irrigation, or the normal drainage flow. Yet the device may readily be maintained in substantially sterile condition and may easily be prepped prior to irrigation.

OBJECTS OF THE INVENTION

An object of this invention is to provide a urinary irrigation device overcoming the aforementioned problems.

Another object of this invention is to provide a urinary irrigation device having a closed irrigation site which is non-complex in structure.

Another object of this invention is to provide a urinary irrigation device having a closed irrigation site which does not impede either the normal drainage flow or the flow of irrigating fluid upon introduction thereof to the system.

Still another object of this invention is to provide a closed irrigation site which is easy to prep prior to irrigation.

Yet another object of this invention is to provide a urinary irrigation device which may readily be maintained in a substantially sterile condition.

Another object of this invention is to provide a closed irrigation site which is adaptable to conventional irrigating syringes.

Yet another object of this invention is to provide a closed irrigation site the operation of which does not cause patient discomfort.

Another object of this invention is to provide a urinary irrigation device which minimizes the likelihood of urinary infection even during long-term catheterization.

Still another object of this invention is to provide a urinary irrigation device which allows substantially sterile irrigation, yet is neither heavy nor bulky.

BRIEF DESCRIPTION OF THE DRAWINGS

These and other objects of the invention will be apparent from the following description of a preferred embodiment wherein:

FIG. 2 is an enlarged perspective view of the urinary irrigation device shown in FIG. 1.

FIG. 3 is a still further enlaged partial side sectional view of the device of FIG. 2, showing the closed irrigation site thereof together with an irrigating syringe and a blunt tip thereof protruding through the irrigation site membrane.

FIG. 4 is a partially exploded perspective view of the urinary irrigation device shown in FIG. 2.

DESCRIPTION OF PREFERRED EMBODIMENTS

Figure 1:
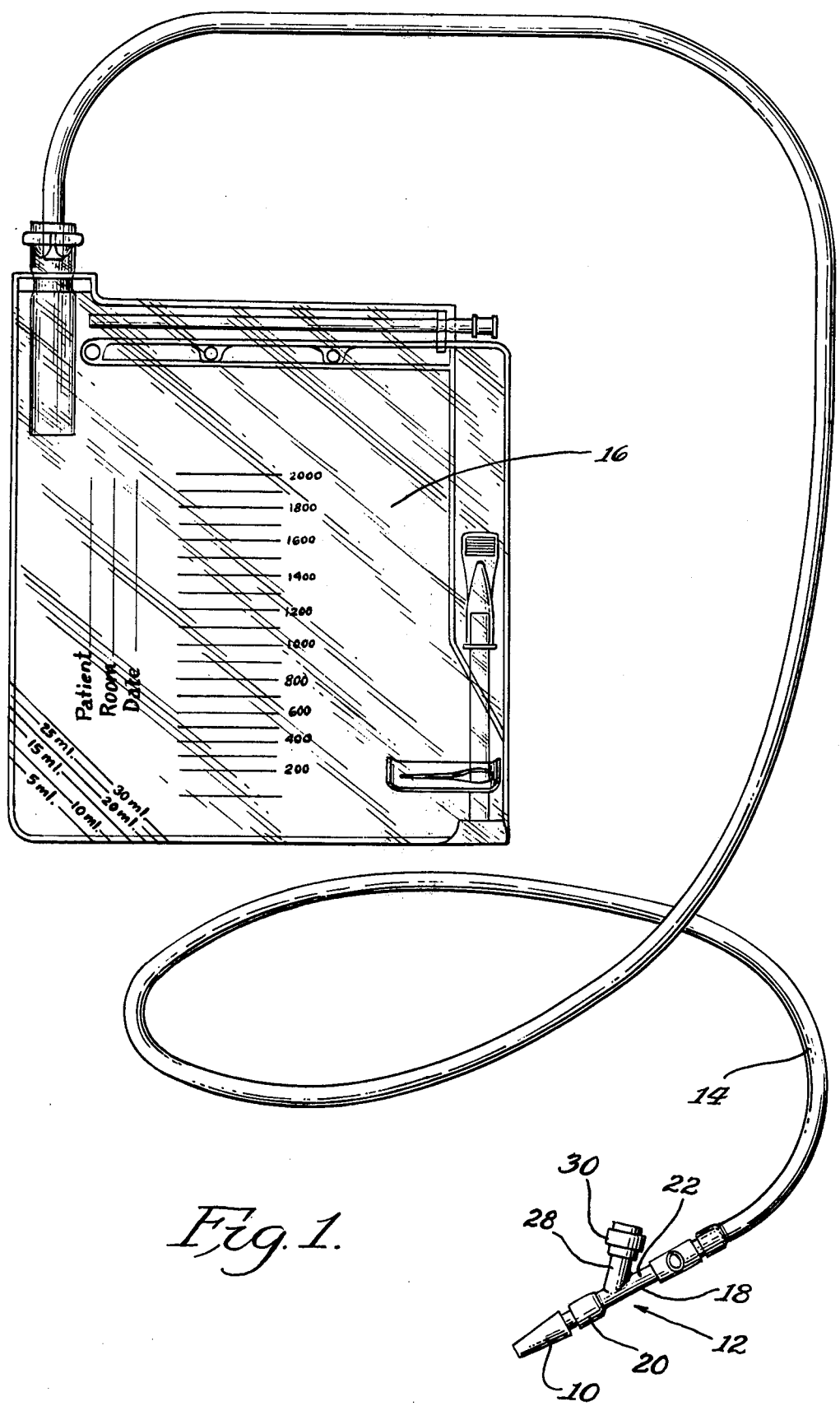
FIG. 1 is a front elevation of a urinary drainage system including the urinary irrigation device of this invention.

FIG. 1 illustrates a urinary drainage system having an adapter member 10 generally at its upstream end, a urinary irrigation device 12 according to this invention in fluid communication with adapter member 10, drainage tubing 14 in fluid communication with urinary irrigation device 12, and collection bag 16 at the downstream end of the system and in fluid communication with drainage tubing 14.

FIGS. 2 and 4 are enlargements of urinary irrigation device 12 and illustrate the parts thereof. Urinary irrigation device 12 has a main tubular member 18 which defines part of a urinary drainage path and extends from an upstream end 20 connected to catheter member 10 to a downstream end 22 connected to drainage tubing 14. The connection of downstream end 22 to drainage tubing 14 is, in the embodiment shown, accomplished through a tubular injection site member 24 which defines a window 26 exposing a latex tube through which minor amounts of various fluids may be introduced by a syringe needle.

Attached to main tubular member 18 is a tubular branch 28 which defines an irrigation path 29 extending to the drainage path from a closed irrigation site 30 at the distal end of branch 28. Tubular branch 28 and main tubular member 18 are an integral, rigid structure which may be made of high density polyethylene, polypropylene, nylon, reinforced polyvinyl chloride, or other suitable rigid materials. Tubular branch 28 forms an obtuse angle with the upstream portion of main tubular member 18, to aid in proper introduction of irrigating fluid.

Closed irrigation site 30 is illustrated best in FIGS. 2, 3 and 4. The distal end of tubular branch 28 includes an enlarged base 32 which projects radially from the axis of the cylinder which forms tubular branch 28. A substantially cylindrical inner annulus 34 projects axially from enlarged base 32 in an upstream direction and terminates in a circular lip 36, which defines a mouth 44 at the end of tubular branch 28. A substantially cylindrical outer annulus 38, which is concentric with and radially spaced from inner annulus 34, projects axially from enlarged base 32 in an upstream direction beyond lip 36. Inner annulus 34 and outer annulus 38 define a substantially cylindrical, annular void 40 therebetween.

A resilient, impervious membrane 42 is secured against lip 36, covering mouth 44 defined by lip 36. Membrane 42 is a resilient, liquid and air impervious member made of latex or other similar material. A wide variety of suitable materials, both natural and synthetic, may be used; materials suitable for membrane 42 will be apparent to those skilled in the art who are familiar with this invention. Membrane 42 is a generally circular, molded member, having a generally cylindrical integral skirt 46. Skirt 46 is received within void 40, which, with lip 36, serves to orient and position membrane 42 within closed irrigation site 30.

A plug member 48 provides means at the distal end of tubular branch 28 to secure membrane 42 against lip 36. Plug member 48 is received into outer annulus 38 and is connected thereto. Plug member 48 defines an axial aperture 50 which provides an access site 52 allowing access to membrane 42. Plug member 48 has an annular end surface 54 which is tapered inwardly toward membrane 42, thereby allowing access site 52 to be readily cleansed by swabbing to prepare for irrigation. Also, the bore of plug member 48 is at least of equal diameter to the bore of inner annulus 34, to avoid the formation of a crevice between plug 48 and membrane 42, analogous to U.S. Pat. No. 3,577,992, which may be a source of contamination.

Membrane 42 has a normally closed, resiliently deformable slit 56 which extends through membrane 42 in a position over mouth 44 at the distal end of tubular branch 28. Slit 56 is substantially straight and membrane 42 is slightly compressed against lip 36, thereby biasing slit 56 to a tight, closed position.

FIGS. 2 and 4 illustrate slit 56 in a closed position. While in the closed position, membrane 42 prevents entry of air into the urinary drainage system. FIG. 3 illustrates slit 56 in a deformed position in which blunt end 56 of syringe 60 protrudes therethrough. In such condition, slit 56 closes about blunt end 58 to prevent entry of air into the urinary drainage system.

While blunt end 58 protrudes through membrane 42, irrigating fluid in syringe 60 may be introduced into the urinary drainage system without any impedance in the closed irrigation site at the point of introduction. The irrigant will flow through tubular branch 28 and into the upstream portion of main tubular member 18 and then through catheter member 10 to the patient's bladder. When blunt end 48 is withdrawn from membrane 42, slit 56 will close upon itself immediately, thereby continuing to protect the urinary drainage system from unnecessary contamination.

Closed irrigation site 30 is substantially free of structural impedance to the normal drainage flow through main tubular member 18 or to the flow of irrigating fluid through tubular branch 28 and main tubular member 18.

Suitable materials for the components of the urinary irrigation device of this invention would be apparent to those skilled in the art who are familiar with this invention. The component parts may be made using readily available materials.

While in the foregoing specification this invention has been described in relation to certain preferred embodiments, and many details have been set forth for purpose of illustration, it will be apparent to those skilled in the art that the invention is susceptible to additional embodiments and that certain of the details herein can be varied considerably without departing from the basic principles of the invention.

What is claimed is:

1. In a urinary irrigation device of the type having a main tubular member defining part of a urinary drainage path and a tubular branch attached thereto and defining an irrigation path extending to said drainage path from a closed irrigation site at the distal end of said branch, the improvement wherein said site comprises:
   a rigid lip defining a mouth at said distal end;
   a resilient, impermeable membrane against said lip and covering said mouth, said membrane having a normally closed, resiliently deformable slit therethrough over said mouth; and
   securing means at said distal end to compress a portion of said membrane, spaced from said slit, against said lip, thereby biasing said slit into a closed position, said biasing effect being greater than that of the uncompressed membrane.

2. The device of claim 1 wherein said securing means forms an annular surface tapered inwardly substantially to said membrane to provide an access site for irrigation which may easily be cleansed to prepare for irrigation.

3. The device of claim 1 wherein said main tubular member and said tubular branch are an integral, rigid structure.

4. The device of claim 1 wherein said distal end includes an enlarged base projecting radially from the axis of said branch, a substantially cylindrical inner annulus projecting axially from said base in an upstream direction to form said lip, a substantially cylindrical outer annulus projecting axially from said base in an upstream direction beyond said lip, said inner and outer annuli defining a substantially cylindrical, annular void therebetween, said membrane having an integral skirt received within said void, and said securing means being an axially apertured plug member received into said outer annulus and connected thereto.

5. The device of claim 4 wherein said plug member has an annular surface tapered inwardly substantially toward said membrane and terminating at said aperture to provide an access site for irrigation which may easily be cleansed to prepare for irrigation.

6. The device of claim 5 wherein said main tubular member and said tubular branch are an integral, rigid structure.

7. The device of claim 1 wherein said slit is substantially straight.

8. The device of claim 6 wherein said branch forms an obtuse angle with an upstream portion of said urinary drainage path.

9. The device of claim 8 wherein said slit is substantially straight.

10. The device of claim 1 in which said rigid lip defines a first bore over which the membrane extends, and said pressing means at the distal end defines a second bore, said bore being of at least the diameter of said first bore and positioned in generally coaxial relation thereto, to avoid the creation of a crevice between said membrane and pressing means capable of harboring contamination when said membrane is pressed inwardly by penetrating means passing through said slit.

11. In a urinary irrigation device of the type having a main tubular member defining part of a urinary drainage path, and a tubular branch attached thereto and defining an irrigation path extending to said drainage path from a closed irrigation site at the distal end of said branch, the improvement comprising:
   a rigid lip defining a mouth at said distal end and a first bore therethrough;
   a resilient impermeable membrane positioned against said lip and covering said mouth and bore, said membrane having a normally closed, resiliently deformable slit therethrough over said mouth; and
   means positioned at said distal end to retain said membrane against said rigid lip, said retaining means defining a second bore, said second bore being of at least the diameter of said first bore, and in generally coaxial relation thereto to avoid creation of a crevice between said membrane and retaining means capable of haboring contamination when said membrane is pressed inwardly with a penetrating member passing through said slit.

12. The urinary irrigation device of claim 1 in which said securing means compresses said membrane in an annular area positioned about said slit.

* * * * *